(12) United States Patent
Wittenberger et al.

(10) Patent No.: US 6,595,988 B2
(45) Date of Patent: Jul. 22, 2003

(54) CRYOTREATMENT DEVICE AND METHOD

(75) Inventors: Dan Wittenberger, Pierrefonds (CA); Claudia Lückge, L'ile-Perrot (CA); Sean Carroll, Beaconsfield (CA)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/887,536

(22) Filed: Jun. 22, 2001

(65) Prior Publication Data

US 2002/0007180 A1 Jan. 17, 2002

Related U.S. Application Data

(60) Provisional application No. 60/213,793, filed on Jun. 23, 2000.

(51) Int. Cl.[7] .......................... A61B 18/18; A61M 29/00
(52) U.S. Cl. .............................. 606/21; 606/20; 606/22; 606/23; 604/101.01
(58) Field of Search .............................. 606/21, 20, 22, 606/23, 25, 26, 27, 28; 604/101.01, 101.02, 101.03, 101.05

(56) References Cited

U.S. PATENT DOCUMENTS

| | | | |
|---|---|---|---|
| 3,173,418 A | * 3/1965 | Baran | 128/207.15 |
| 4,328,056 A | * 5/1982 | Snooks | 156/242 |
| 5,049,132 A | * 9/1991 | Shaffer et al. | 604/101.02 |
| 5,458,575 A | * 10/1995 | Wang | 604/101.02 |
| 5,536,252 A | 7/1996 | Imran et al. | 604/101 |
| 5,704,913 A | 1/1998 | Abele et al. | 604/101 |
| 5,868,735 A | 2/1999 | Lafontaine | 606/21 |
| 5,902,299 A | 5/1999 | Jayaraman | 606/20 |
| 5,971,979 A | 10/1999 | Joye et al. | 606/21 |
| 6,136,011 A | * 10/2000 | Stambaugh | 604/101.02 |
| 6,254,570 B1 | * 7/2001 | Rutner et al. | 604/101.01 |
| 6,290,696 B1 | * 9/2001 | Lafontaine | 606/21 |
| 6,355,029 B1 | * 3/2002 | Joye et al. | 606/21 |

FOREIGN PATENT DOCUMENTS

| | | |
|---|---|---|
| FR | 2600205 A1 | 5/1987 |
| WO | WO 00/54684 | 9/2000 |

* cited by examiner

Primary Examiner—Linda C. M. Dvorak
Assistant Examiner—Kenneth G Schopfer
(74) Attorney, Agent, or Firm—Christopher & Weisberg, PA

(57) ABSTRACT

A medical device for cryotreatment of bodily regions is disclosed. The device comprises an inflatable support structure coupled to the distal end portion of a catheter shaft, the support structure being further enveloped by an expandable membrane to define an expansion chamber between the support structure and the membrane. An inflation lumen is coupled to the support structure to inject an inert, insulating fluid in the support structure, thereby expanding the support structure and the expandable membrane, wherein the resultant expansion chamber formed therebetween is substantially conical in shape. Refrigerant is injected into the expansion chamber, thereby creating localized cooling of tissues adjacent to the expansion chamber, the cooling region being substantially conical in shape. Alternately, a second inflatable support structure is provided inside of the expandable membrane and distal to the first support structure, to define an expansion chamber therebetween that is substantially toroidal in shape, thereby enabling the creation of circumferential cooling regions when refrigerant is injected into said expansion chamber.

26 Claims, 2 Drawing Sheets

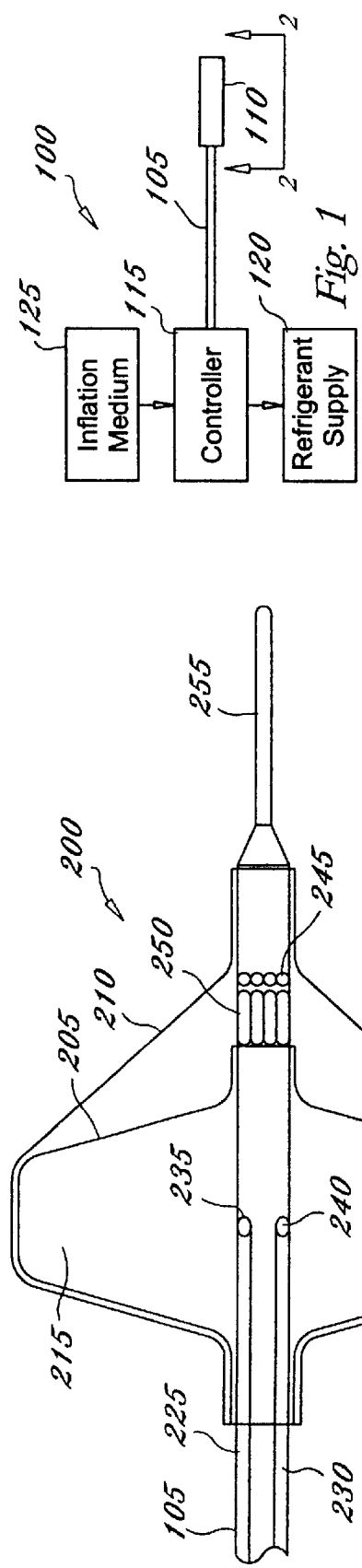
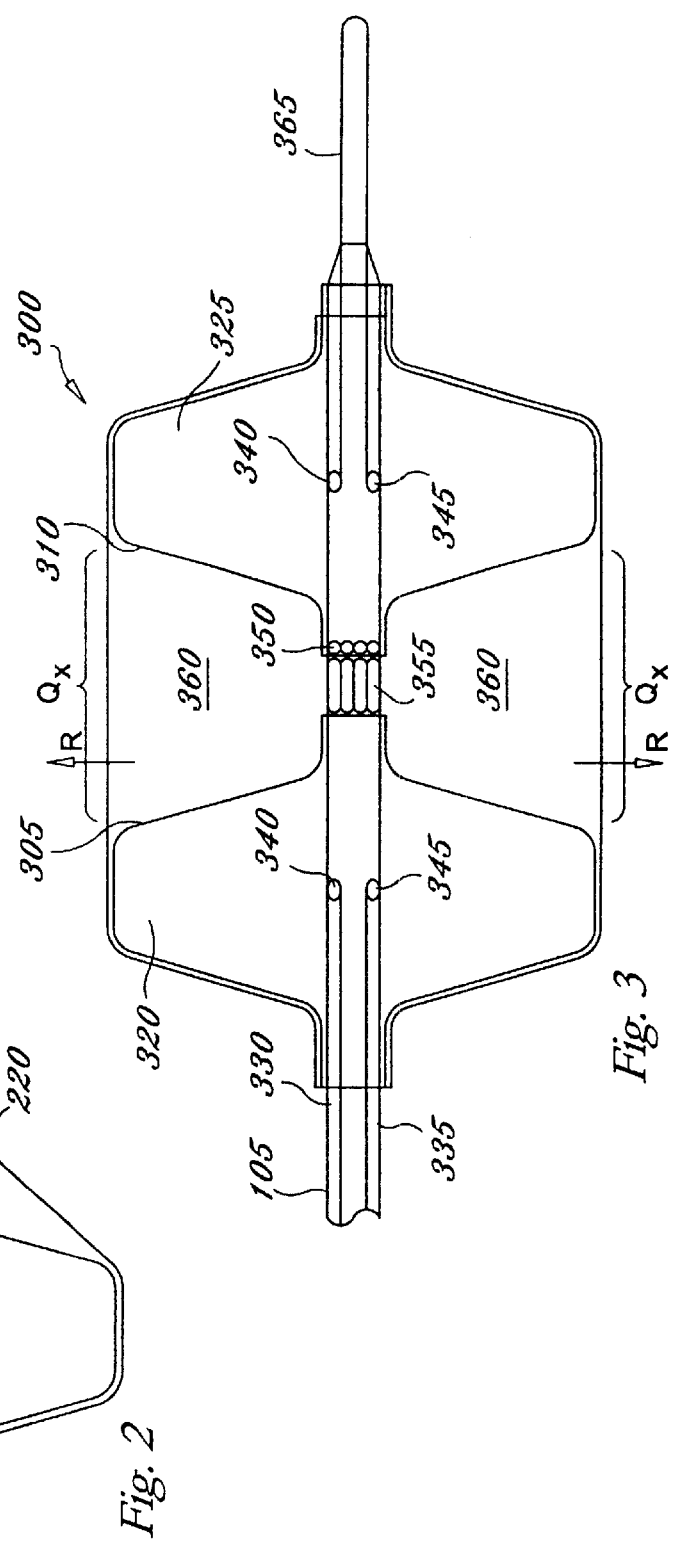

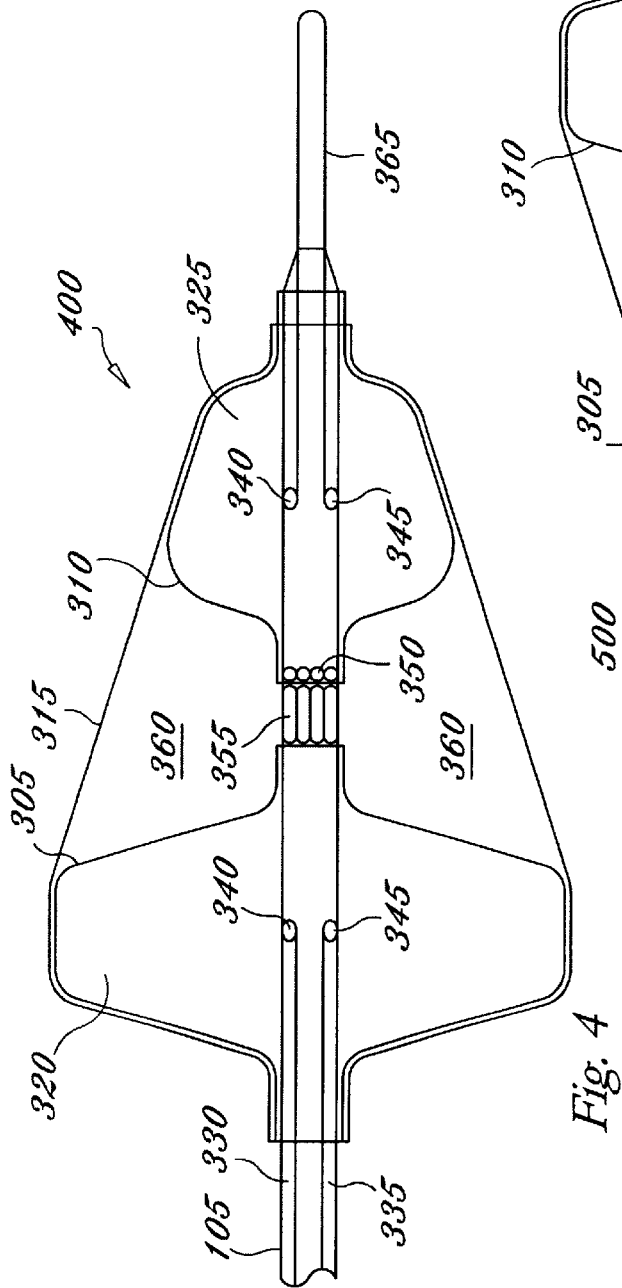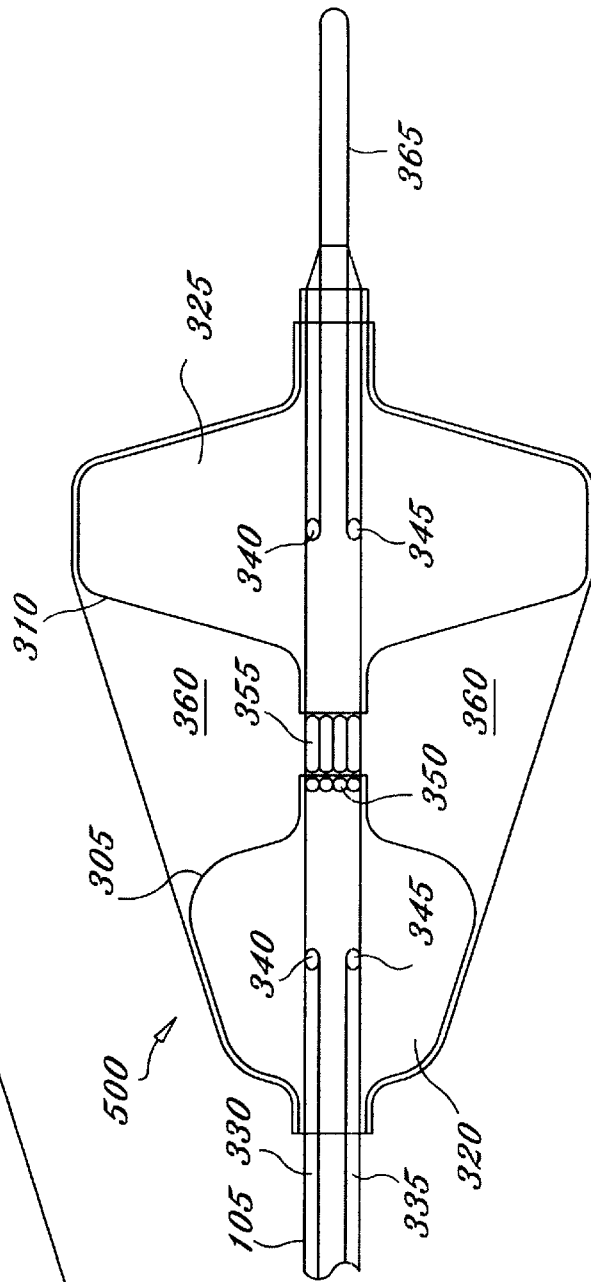

CRYOTREATMENT DEVICE AND METHOD

CROSS-REFERENCE TO RELATED APPLICATION

This application is related to and claims priority to U.S. Patent Application Serial No. 60/213,793, filed Jun. 23, 2000, entitled SUPPORT FOR AN EXPANDABLE MEMBRANE, the entirety of which is incorporated herein by reference.

STATEMENT REGARDING FEDERALLY SPONSORED RESEARCH OR DEVELOPMENT n/a

FIELD OF THE INVENTION

The present invention relates to medical devices, and in particular, to balloon catheter devices which employ cryogenic fluids to treat complex three-dimensional surfaces.

BACKGROUND OF THE INVENTION

Recently, the use of fluids with low operating temperatures, i.e. cryogenic fluids or refrigerants, has begun to be explored in the medical and surgical field. Of particular interest are the potential use of catheter based devices, which employ the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible.

A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. The quality and magnitude of heat transfer is regulated by device configuration and control of the refrigerant flow regime within the device.

Structurally, cooling can be achieved through injection of high pressure refrigerant through an orifice. Upon injection from the orifice, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

Once refrigerant is injected through an orifice, it may be expanded inside of a closed expansion chamber which is positioned proximal to the target tissue. The resulting heat transfer thus occurs across a surface generally defined by the contact area between the medical device and the target tissue, thereby forming "lesions" on the target tissue. Such lesions conform to the particular geometry of the portion of the medical device being cooled by the flow of refrigerant therethough. In other words, the size and shape of the tissue treated is analogous to the geometry of the expansion chamber wherein refrigerant is injected in the medical device. Medical devices which employ such refrigerant injection techniques vary as to size and shape. Devices wherein an expandable membrane, similar to an angioplasty balloon, are employed as expansion chambers, have recently been explored. In such a device, refrigerant is supplied through a catheter tube into an expandable balloon coupled to such catheter, wherein the refrigerant acts to both: (i) expand the balloon near the target tissue for the purpose of positioning the balloon, and (ii) cool the target tissue proximal to the balloon to cold-treat adjacent tissue.

The principal drawback to such a technique is that the balloon geometry is generally spherical or ellipsoidal, as the flexible membrane comprising the balloon either expands in a uniform radial direction, or expands to conform to the geometry of the tissue next to which it is positioned. In both cases, the surface geometry of the expanded membrane does not ideally conform to the surface geometry of the tissue to be treated. Most devices can only form either linear, circular, or spherical lesions, while the desired lesion geometry may be highly complex. This is especially true in the case of body ostia, such as the junctions between arteries or veins and chambers of the head and neck, wherein the surface geometry of the tissue to be treated is either conical, cylindrical, or more often, a complex three-dimensional surface, or some combination thereof.

It is therefore desirable to provide a medical device which maximizes the efficiency of cryogenic cold-treatment, by providing a treatment surface area which is well-suited to create lesions which conform to conical, cylindrical, or other complex three-dimensional surfaces. It is further desirable to provide such a medical device, wherein the size, shape, and geometry of the treatment surface is controllable during operation of the device and consequent cooling of tissue adjacent thereto.

SUMMARY OF THE INVENTION

The medical device comprises a first expandable support structure transitionable from a first to a second state, and an expandable membrane enveloping the first support structure to define an expansion chamber when the support structure is in the second state.

In a first embodiment of the invention, the device includes an elongate shaft having proximal and distal end portions, the shaft defining an injection lumen, an exhaust lumen, and an inflation lumen therethrough, each lumen having a proximal end portion and distal end portion proximate the proximal and distal end portions of the shaft, respectively. An expandable support structure is coupled to the distal end portion of the shaft, having an inner surface and an outer surface, the inner surface being in fluid communication with the distal end portion of the inflation lumen to define an inflation chamber inside of the membrane. An expandable membrane having an inner surface and an outer surface is disposed around the support structure, the inner surface being in fluid communication with the distal end portions of the injection and exhaust lumens, to define an expansion chamber between the support structure and the expandable membrane. The inflation lumen is coupled to a supply of inflation medium, whereas the injection lumen is coupled to a supply of refrigerant, wherein after the expandable support structure is inflated by the injection of inflation medium therein, refrigerant is injected into the expansion chamber inside of the expandable membrane, to cool the region adjacent to and surrounding the device proximate to the expansion chamber.

In another embodiment of the invention, both the expandable support structure and the expandable membrane are fluidly coupled to the refrigerant injection and exhaust lumens such that refrigerant may flow throughout both the inflation chamber and the expansion chamber. In a particular application of such an embodiment, the expandable support structure may be injected with refrigerant, while the expandable membrane enveloping the support structure may be actively coupled to the exhaust lumen only, such that vacuum conditions exist in the expansion chamber, whereby the expandable membrane effectively serves as a negative apposition device around the expandable support structure.

In another embodiment of the invention, two expandable membranes are disposed on the distal end portion of the catheter shaft, surrounded by a third expandable membrane to define an expansion between the first two membranes that is substantially toroidal or cylindrical when the first two membranes are inflated by the injection of inflation medium therein. Refrigerant is thereafter injected into the expansion chamber to cool regions immediately adjacent to and outside of the third membrane of the device, proximate to the expansion chamber.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is a schematic diagram of a system that includes a medical device in accordance with the present invention;

FIG. 2 is a longitudinal cross-sectional view of the distal portion of the device shown in FIG. 1, taken along line 2—2;

FIG. 3 is a longitudinal cross-sectional view of the distal portion of an alternate arrangement of the device which is part of the system shown in FIG. 1;

FIG. 4 is a longitudinal cross-sectional view of the distal portion of an alternate configuration of the device arrangement shown in FIG. 3, which is part of the system shown in FIG. 1; and FIG. 5 is a longitudinal cross-sectional view of the distal portion of another configuration of the device arrangement shown in FIG. 3, which is part of the system shown in FIG. 1.

DETAILED DESCRIPTION OF THE INVENTION

As used herein, the term "refrigerant" or "cryogenic fluid" refers to a fluid substance with properties suitable for: (i) steady flow through ducts of small diameter, (ii) high pressure compression into liquid phase, and (iii) evaporation and expansion to gas phase at low temperatures, typically below zero degrees centigrade. The refrigerant may be any suitable, relatively inert "working fluid", such as nitrogen, nitrous oxide, or carbon dioxide, or refrigerants such as chlorodifluoromethane, ethyl alcohol, or Freon (a trademark of DuPont), or any number of other refrigerants or mixtures thereof with a high thermal energy transfer capacity and low boiling point, as are commonly known to those skilled in the art.

As used herein, the term "tube" refers to an elongate duct or conduit suitable for conveying a fluid. The tube may comprise any number of elements or members, and may have a varying range of properties and dimensions, such as length, thickness, and cross-sectional shape. The term "lumen" refers to the elongate passageway defined by a tube, suitable for the flow of fluid therein.

As used herein, for a particular region or space with fluid flowing therein, the term "downstream" refers to the relative spatial direction equivalent to the direction of the macroscopic flow of such fluid in such region or space.

Also as used herein, the term "catheter" refers to a medical device composed of any number of tubes and ancillary structures, for insertion into canals, vessels, passageways or other body cavities to permit the treatment of body tissue proximate to the catheter. A catheter may be constructed from a variety of suitable materials having a varying range of structural and thermal properties. It is understood that the particular structural, dimensional, and/or thermal properties of a catheter included in the present invention may considerably vary depending on the particular application of the device disclosed herein.

Finally, as used herein, the term "membrane" refers to a thin sheet structure having a very high surface area to volume ratio, an inner surface, and an outer surface, similar to that of a balloon. The term "expandable", when applied to a membrane, refers to the membrane's ability to go from a non-tensioned or "collapsed" first state to a tensioned or "stretched" second state, in response to the pressures created by the expansion of a fluid therein, whether or not this involves elastic deformation of said membrane.

Referring now to the drawings, in which like reference designators refer to like elements, there is shown in FIG. 1 a schematic representation of a system constructed in accordance with the principles of the present invention, and designated generally as 100. System 100 includes a catheter 105 having a distal tip assembly 110, a controller unit 115, a cryogenic fluid supply 120, and an inflation medium supply 125. The system 100 may also include, although the operation of the overall device and invention does not so require, a user interface or console coupled to the controller unit 115.

In the alternative, the system 100 need not include an inflation medium supply 125, such that only cryogenic fluid is supplied to the catheter 105 and the tip assembly 110. Furthermore, the system 100 may be integrated and coupled to one of the following catheter based devices, as is well-known to those skilled in the art: (i) a deflectable catheter system, wherein the catheter 105 includes deflection wires or other suitable members or means for deflecting the tip assembly 110 in response to a user command or mechanical input at the proximal end of the catheter system; (ii) a conventional "over-the-wire" catheter system and device; or (iii) a "rapid exchange" catheter system.

Either the controller unit 115 or such user console is employed to control the operation of the device and the flow of fluid therethrough. The controller unit 115 is preferably composed of any number of suitable mechanical or electronic device components that are capable of receiving and executing programmed instructions, sensor signals, or manual user input as is known in the art. The controller unit 115 may comprise, without limitation, any of the following components: (i) a computer or microprocessor, (ii) a flow pump and vacuum pump, (iii) a filter or fluid filtration system, (iv) a feedback, closed-loop, or open-loop control system, including all mechanical and electrical components customarily used in such control systems, (v) any number of pressure and temperature sensors, or (vi) any of the commonly used devices for controllably dispensing and receiving fluid flows in a closed-loop flow system wherein the mass flow rate, temperature and pressure of the fluid flow is monitored and regulated.

As shown in FIG. 1, the controller unit 115 is coupled to the flow of cryogenic fluid from the refrigerant supply 120, wherein the controller unit 115 directs and regulates the flow of cryogenic fluid into the catheter 105. During application of the device, the catheter 105 is introduced into a body and the distal tip assembly 110 is placed in contact with or proximate to selected tissue. Cryogenic fluid is then directed to flow to the distal tip assembly 110, whereupon the fluid undergoes a gas dynamic expansion and evaporation process, thereby cooling portions of the distal tip assembly 110 to low temperatures for selectively cold-treating surrounding tissue.

The refrigerant supplied may be either in a liquid or a gaseous state, or a mixture thereof. The refrigerant is cooled and/or compressed to a predetermined initial temperature and initial pressure before introduction into the catheter 105. Catheter 105 contains multiple tubes (not shown), preferably made of flexible or rigid material such as a polymer, fiber, metal, or any combination thereof. The tubes are arranged to create a plurality of lumens (not shown) for the flow of refrigerant therethrough. These lumens are arranged to create a closed-loop circulation path for the flow of refrigerant through the device. This includes an injection lumen (not shown) through which the refrigerant is introduced into catheter 105, and flows therethrough from the supply 120 through to the distal tip assembly 110; and a return lumen (not shown), through which refrigerant eventually flows back to the controller unit 115 from the distal tip assembly 110. The controller unit 115 is further used to create vacuum pressure conditions (or negative gauge pressure) at the proximal portion of the return lumen. The initial supply pressure of the refrigerant is preferably on the order of 30 to 55 atmospheres, or 400 to 800 psia, much higher than the eventual final pressure in the vacuum return lumen. The resultant negative pressure gradient drives the high pressure refrigerant drawn from supply 120 to flow through the injection lumen in catheter 105, to the distal tip assembly 110, and thereafter back through the return lumen.

Catheter 105 further includes at least one each of an inflation lumen and an exhaust lumen (not shown) which fluidly couple the supply of inflation medium 125 with the distal tip assembly 110. The same pressure regulation device used in the controller 115 to regulate the flow of refrigerant may also be used to regulate the flow of inflation medium. The inflation medium may be any inert, non-toxic fluid commonly used to inflate angioplasty-type balloons, such as saline, and may further be laced with a radiographically opaque contrast medium to enable radiographic-mapping of the target tissue during application and operation of the device. In addition, the inflation medium may be comprised of a fluid having a relatively low thermal conductivity such that it acts as an insulation medium as well as an inflation medium.

In the alternative, the inflation medium may also be a refrigerant, similar or identical to the refrigerant used in the refrigerant supply 120. In such an embodiment, as specified above, the system 100 of FIG. 1 does not include a separate inflation medium supply 125. Rather, the catheter 105, along with the inflation and exhaust lumens (otherwise used for the injection and removal of a separate inflation medium), are fluidly coupled the refrigerant supply 120 only.

FIG. 2 shows a longitudinal cross-sectional view of an exemplary embodiment of the present invention, illustrating, namely, the distal end portion of catheter 105, including the distal tip assembly 110 of FIG. 1, generally designated in FIG. 2 as 200. In this embodiment of the present invention, the distal tip assembly 200 shown in FIG. 2 comprises an inner membrane 205, an outer membrane 210, an inflation chamber 215, an expansion chamber 220, at least one inflation lumen 225, at least one exhaust lumen 230, at least one inflation orifice 235, at least one exhaust orifice 240, at least one injection lumen (not shown), at least one return lumen (not shown), a plurality of injection orifices 245, a plurality of vacuum orifices 250, and a guidewire 255.

Both the inner membrane 205 and outer membrane 210 are expandable balloon-like structures, coupled to the distal end of the catheter shaft 105, as shown in FIG. 2. FIG. 2 illustrates the geometric state of the inner membrane 205 and outer membrane 210, when the inner membrane 205 is inflated with the inflation medium. In such a state, the inner membrane 205 defines an inflation chamber 215 therein, and further defines an expansion chamber 220 between inner membrane 205 and outer membrane 210.

The inner membrane 205 is fluidly coupled to the inflation lumen 225 and exhaust lumen 230 via the inflation orifice 235 and exhaust orifice 240, respectively. Inflation medium is controllably injected into inner membrane 205 through injection orifice 235, thereby creating an inflation chamber 215 having a radial axis of symmetry coincident or parallel to the longitudinal axis of symmetry of catheter 105. Alternatively, the coupling and geometric expansion characteristics of inner membrane 205 to catheter 110 may be varied to allow for the formation of a variety of inflation chamber 215 volumes and shapes, and need not be axisymmetric as shown in FIG. 2. The size and shape of the inflation chamber 215 created by the injection of inflation medium may be controlled by use of either (i) a pressure monitor (not shown), such as a piezo-electric pressure gauge or an optical pressure transducer in fluid communication with the inflation chamber 215, (ii) a radiographic mapping device to view the inflation chamber 215 inside of a body when a contrast medium is employed with the inflation medium, or (iii) by use of cryogenic fluid instead of the inflation medium, such that refrigerant is controllably injected into the inflation chamber 215 using the controller 115 of FIG. 1. The inner membrane 205 is deflated by controllably exhausting the inflation medium or refrigerant, as the case may be, through exhaust orifice 240 and exhaust lumen 230.

As shown in FIG. 2, inner membrane 205 is positioned inside of outer membrane 210, such that when inner membrane 205 is inflated, it acts as a support structure to inflate the outer membrane 210. Both inner membrane 205 and outer membrane 210 may be pre-formed to conform to a given geometry when inflated. As shown in FIG. 2, inner membrane 205 has a shorter longitudinal length that outer membrane 210, but an equal radius. This serves to create a conical expansion chamber 220 between the two membranes when the inner membrane 205 is inflated.

In an alternative arrangement of this embodiment of the invention, inner membrane 205 may be replaced by a mechanical support structure that essentially functions exactly the same as element 205, in that it is transitionably expandable from a first state to a second state, the second state being of significantly greater volume and diameter than the first state. In such an arrangement, only the particular material and mechanical properties of element 205 are changed. The formation of a conical expansion chamber 220, and subsequent flow of refrigerant therethrough, as elaborated below, as identical to previously discussed embodiments, and the cryotreatment characteristics of the present invention are essentially the same.

After inflation, refrigerant is supplied through an injection lumen (not shown) in the catheter shaft 105, the refrigerant being injected into the expansion chamber 220 through the injection orifices 245. The outer membrane 210 is also in fluid communication with vacuum orifices 250, whereby refrigerant injected into the expansion chamber 220 thereafter flows through the vacuum orifices 250, into a return lumen (not shown) and back towards the controller unit 115. The "spent" refrigerant vapor is either: (i) vectored back to the controller unit 115 or refrigerant supply 120 for recycling of the refrigerant in a closed-loop flow arrangement, or (ii) discarded from the device in an open-loop flow arrangement.

The distal tip assembly may further include a guidewire 255 positioned either through a guidewire lumen (not shown) inside of catheter shaft 105, or affixed to the distal end of the tip assembly to provide for ease of positioning of the device in a body, such guidewire configurations being well known to those skilled in the art.

As refrigerant is injected into expansion chamber 220, it undergoes both an evaporative process, whereby liquid-phase refrigerant is evaporates into gas-phase, thereby absorbing latent heat of vaporization, and a Joule-Thomson throttling process, whereby gas-phase refrigerant is cooled to a very low temperature. Both processes act to lower the temperature of the refrigerant flowing through the expansion chamber 220 to the range of zero to –140 degrees Centigrade. The low temperature refrigerant in the expansion chamber 220 thereby acts to cool any tissue adjacent to or proximate the outer surface of the expansion chamber 220.

Since the expansion chamber 220 is conical in shape, the target region of tissue to be cooled will also be conical in shape, allowing a user of the device to form circumferential lesions of varying circumference, much like a cone or frustrum of a cone. This is especially useful for body tissues comprising an ostium, since the conical shape of the outer membrane 210 allows for optimal placement of the device in such an ostium. Only the desired tissue surface area is cold-treated by the contact of expansion chamber 220. The particular arrangement of the membranes shown in FIG. 2 may also be varied to create conical expansion chambers of varying radius and longitude to optimally fit the desired region of tissue to be cold-treated.

As discussed above, the embodiment of FIG. 2 may be alternatively employed to function using refrigerant instead of a separate inflation medium inside of the inflation chamber 215. In such an arrangement of the present invention, inflation lumen 225 and exhaust lumen 230 are instead injection and vacuum exhaust lumens, respectively, allowing for the fluid injection and vacuum exhaust of refrigerant therethrough. In such an arrangement, refrigerant inflates or expands membrane 205 and occupies inflation chamber 215. Refrigerant may also be simultaneously injected into expansion chamber 220, thereby providing a double-walled refrigerant-filled membrane at the end of the catheter 105.

In yet another arrangement of the invention, refrigerant may be injected into inflation chamber 215, while no fluid is injected into expansion chamber 220. Instead, the injection orifices 245 are sealed, while the expansion chamber is in fluid communication with the vacuum orifices 250 and vacuum exhaust lumens coupled thereto (not shown). The outer membrane 210 is thus supported by the inflation and expansion of the inner member 205, such that the outer membrane 210 effectively wraps around the outer surface of inner member 205, the volume of the expansion chamber 220 being minimal due to vacuum pressure conditions therein. In such an arrangement, the refrigerant flows throughout the inflation chamber 215, providing the desired cooling to tissues adjacent to the device. The refrigerant is contained by inner member 205, while outer member 210 serves to further contain the fluid flow inside the apparatus. If the inner member 205 should leak or rupture, then the presence of the vacuum in space 220 acts to draw any free fluid outside of member 205 into the exhaust lumen coupled to the vacuum orifices 250. In such an arrangement, member 210 effectively serves as a negative apposition device which contains and preserves the flow of refrigerant throughout the catheter, and prevents the undesired leakage of refrigerant into the environment immediately surrounding the device.

Another exemplary embodiment of the present invention is illustrated in FIG. 3. FIG. 3 also shows the distal tip assembly 110 of FIG. 1, designated generally as 300. Distal tip assembly 300 comprises a proximal inner membrane 305, a distal inner membrane 310, an outer membrane 315, a proximal inflation chamber 320, a distal inflation chamber 325, at least one inflation lumen 330, at least one exhaust lumen 335, a plurality of inflation orifices 340, a plurality of exhaust orifices 345, at least one injection orifice 350, at least one vacuum orifice 355, an injection lumen (not shown), a return lumen (not shown), an expansion chamber 360, and a guidewire 365.

In this embodiment, two expandable membranes 305 and 310 are coupled to the catheter shaft 105 and are surrounded by an outer membrane 315, as shown in FIG. 3. Both of the inner membranes 305 and 310 are controllably inflated by an inflation medium flowing from the inflation lumen 330, through the inflation orifices 340, and into the respective inflation chambers 320 and 325, defined by the proximal inner membrane 305 and distal inner membrane 310, respectively, as such membranes expand and inflate. Once the inner membranes 305 and 310 are inflated as shown in FIG. 3, an expansion chamber 360 is formed therebetween inside of the outer membrane 315. Refrigerant is thereafter injected into the expansion chamber 360 via the injection orifices 350 and flows back out of the expansion chamber 360 via the vacuum orifices 355. As in the previous embodiment shown in FIG. 2, the flow of low temperature refrigerant through the expansion chamber 360 acts to cool any tissue adjacent to or proximate such expansion chamber 360. Because the expansion chamber 360 is shaped like an annulus or toroid, the heat transfer between the tissue and expansion chamber 360 occurs across the surface of the outer membrane 315 which lies between the proximal and distal inner membranes 305 and 310, designated in FIG. 3 as QX. This geometry focuses the cooling power of the device on such an annular surface area, whereby heat transfer occurs primarily in the radial direction R shown in FIG. 3, and not in the direction perpendicular to the radial direction R. This allows for the formation of circumferential lesions that are substantially cylindrical, and are confined to the annular band defined by the surface area of expansion chamber 360 in contact with adjacent tissue.

FIG. 4 shows an alternate configuration of the embodiment shown in FIG. 3, designated generally as 400, whereby the distal inner membrane 310 is inflated to a size smaller than that of the proximal inner membrane 305. This serves to create another toroidal annular expansion chamber 360, but with a radius of decreasing size towards to distal end of the device. Each of the inner membranes 305 and 310 may be alternately controllably inflated via inflation orifices 340 to create inflation chambers 320 and 325 of varying shape, thereby creating expansion chambers 360 of varying radius and longitudinal size. This allows the device to conform to a variety of complex tissue geometries, and further allows the device to be optimally positioned in such regions, whereby each of the inner and outer membranes 305 and 310 may be inflated in situ using a contrast medium with the inflation medium for external monitoring and positioning of the device.

FIG. 5 shows yet another configuration of the embodiment shown in FIG. 3, designated generally as 500, whereby the distal inner membrane 310 is inflated to a size larger than that of the proximal inner membrane 305. This embodiment effectively functions much the same as the embodiment shown in FIG. 4, except that the expansion chamber 360 has a radius of increasing size in the distal direction. In both of the configurations shown in FIGS. 4 and 5, the smaller inner membrane may deflated to minimum size, thereby creating a conical expansion chamber 360, very similar in shape to that of the expansion chamber 220 shown in FIG. 2.

As discussed previously with respect to the embodiment of FIG. 2, each of the device configurations of FIGS. 3–5 may be employed using a cryogenic fluid or refrigerant instead of an inflation medium to both inflate and support members 305 and 310 as well as occupy chambers 320 and 325. In such an alternate arrangement, refrigerant instead of inflation medium is employed to inflate members 305 and 310, while refrigerant may be withheld from expansion chamber 360, thereby reversing the spatial orientation of cooling fluid flow, and resultant heat transfer and cooling patterns, of the device. This is achieved by using inflation lumens 330 and exhaust lumens 335 as injection and vacuum lumens, respectively, for the flow of refrigerant therethrough. While refrigerant is injected into chambers 320 and 325, the device may be operated either by: (i) injecting an inert insulating fluid into expansion chamber 360 so as to focus and contain cooling outside of and immediately adjacent to (rather than through) surface QX shown in FIG. 3, thereby creating a dual annular circumferential cooling surface for cryotreatment, separated by the distance QX; or, (ii) not injecting any fluid into expansion chamber 360, and instead maintaining a vacuum therein by use of vacuum orifices 355, so as to create a negative apposition membrane in element 315, which acts to contain and fluidly insulate the inner members 305 and 310 from rupture and resultant leaking of refrigerant.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    a first support structure transitionable from a first shape to a second shape;
    an expandable membrane enveloping the first support structure to define an expansion chamber when the support structure is in the second shape;
    a supply of cryogenic fluid in fluid communication with the expansion chamber; and
    a supply of inflation fluid in fluid communication with the first support structure.

2. The device according to claim 1, wherein the expansion chamber is substantially conical in shape.

3. The device according to claim 1, further comprising a second support structure transitionable from a first state to a second state, the expandable membrane enveloping both the first and second support structure such that the expansion chamber is defined between the first and second support structures when such support structures are in their respective second states.

4. The device according to claim 3, wherein the expansion chamber is substantially toroidal in shape.

5. The device according to claim 1, wherein the first support structure is continuously transitionable between the first and second state, to define a continuously transitionable expansion chamber, the expansion chamber having a minimum and maximum volume when the support structure is in its first and second states, respectively.

6. The device according to claim 1, wherein the device is coupled to and integrated into a deflectable catheter system.

7. The device according to claim 1, wherein the device is coupled to and integrated into an over-the-wire catheter system.

8. The device according to claim 1, wherein the device is coupled to and integrated into a rapid exchange catheter system.

9. A medical device comprising:
    an elongate shaft having proximal and distal end portions, the shaft defining or containing an injection lumen, an exhaust lumen, and an inflation lumen therethrough, each lumen having a proximal end portion and distal end portion proximate the proximal and distal end portions of the shaft, respectively,
    a first expandable membrane coupled to the distal end portion of the shaft, having an inner surface and an outer surface, the inner surface being in fluid communication with the distal end portion of the inflation lumen to define an inflation chamber inside of the membrane,
    a second expandable membrane having an inner surface and an outer surface, the inner surface being in fluid communication with the distal end portions of the injection and exhaust lumens, the second membrane being disposed around the first membrane to define an expansion chamber therebetween,
    a supply of cryogenic fluid in fluid communication with the proximal end portion of the injection lumen, wherein the injection lumen, expansion chamber, and exhaust lumen define a fluid path for the flow of cryogenic fluid therethrough, and
    a supply of inflation fluid in fluid communication with the proximal end portion of the inflation lumen, wherein the inflation lumen and inflation chamber define a fluid path for the flow of inflation fluid therethrough.

10. The device according to claim 9, wherein the first expandable membrane is filled with inflation fluid, the inflation fluid being in contact with the inner surface of the first expandable membrane.

11. The device according to claim 10, wherein the second expandable membrane is filled with cryogenic fluid, the cryogenic fluid being in contact with the outer surface of the first expandable membrane and the inner surface of the second expandable membrane.

12. The device according to claim 9, wherein the first expandable membrane is transitionable from a first geometric shape to a second geometric shape, to define a first geometric shape and a second geometric shape, respectively, of the expansion chamber.

13. The device according to claim 12, wherein the second geometric shape of the first expandable membrane is substantially cylindrical, such that the second geometric shape of the expansion chamber is substantially a frustum of a right circular cone, the expansion chamber being distal to the first expandable membrane, the first expandable membrane and the expansion chamber each sharing an axis of radial symmetry parallel to the distal end portion of the elongate shaft.

14. The device according to claim 9, wherein the cryogenic fluid is nitrous oxide.

15. The device according to claim 9, wherein the inflation fluid is saline solution.

16. The device according to claim 9, wherein the cryogenic fluid is nitrogen.

17. A medical device comprising:
an elongate shaft having proximal and distal end portions, the shaft defining or containing an injection lumen, an exhaust lumen, and an inflation lumen therethrough, each lumen having a proximal end portion and distal end portion proximate the proximal and distal end portions of the shaft, respectively, a first expandable membrane coupled to the distal end portion of the shaft, having an inner surface and an outer surface, the inner surface being in fluid communication with the distal end portion of the inflation lumen to define an inflation chamber inside of the membrane, a second expandable membrane having an inner surface and an outer surface, the inner surface being in fluid communication with the distal end portions of the injection and exhaust lumens, the second membrane being disposed around the first membrane to define an expansion chamber therebetween, a supply of cryogenic fluid in fluid communication with the proximal end portion of the injection lumen, wherein the injection lumen, expansion chamber, and exhaust lumen define a fluid path for the flow of cryogenic fluid therethrough, and a vacuum lumen defined or contained in the shaft, the vacuum lumen being in fluid communication with the inflation chamber, the supply of cryogenic fluid being in fluid communication with the inflation and vacuum lumens, wherein the inflation lumen, inflation chamber and vacuum lumen define a fluid path for the flow of cryogenic fluid therethrough.

18. A method for cooling a cryogenic medical device, including the steps of:
a) providing a supply of cryogenic fluid;
b) fluidly connecting said supply of cryogenic fluid with a catheter containing an injection lumen, an exhaust lumen, and a vacuum lumen therein, the catheter and lumens having corresponding proximal and distal ends, the catheter having an expandable support structure coupled to its distal end in fluid communication with the injection lumen and exhaust lumen, and having an expandable membrane coupled to the distal end, the expandable membrane enveloping the support structure to define an expansion chamber therebetween, the expandable membrane being fluid communication with the vacuum lumen;
c) providing a flow regulation system to dispense cryogenic fluid into the injection lumen to inflate the expandable support structure from a first geometric state to a second geometric state;
d) providing a flow regulation system to maintain vacuum pressure in the expansion chamber inside of the expandable membrane;
e) controllably evacuating the cryogenic fluid from the expandable support structure through the exhaust lumen.

19. A medical device comprising:
a first support structure transitionable from a first shape to a second shape; and
an expandable membrane enveloping the first support structure to define an expansion chamber when the support structure is in the second shape; wherein said second shape of said first support structure is substantially cylindrical, such that the expansion chamber is substantially a frustum of a right circular cone, the expansion chamber being distal to the first support structure;

a supply of expansion fluid in fluid communication with the expansion chamber; and a supply of inflation fluid in fluid communication with the first support structure.

20. The device according to claim 19, wherein the inflation fluid is a cryogenic fluid.

21. The device according to claim 19, wherein the expansion fluid is a cryogenic fluid.

22. A medical device comprising:
an elongate shaft having proximal and distal end portions, the shaft defining or containing an injection lumen, an vacuum lumen, and an inflation lumen therethrough, each lumen having a proximal end portion and distal end portion proximate the proximal and distal end portions of the shaft, respectively, a first expandable membrane coupled to the distal end portion of the shaft, having an inner surface and an outer surface, the inner surface being in fluid communication with the distal end portion of the inflation lumen to define an inflation chamber inside of the membrane, a second expandable membrane having an inner surface and an outer surface, the inner surface being in fluid communication with the distal end portions of the injection and vacuum lumens, the second membrane being disposed around the first membrane to define an expansion chamber therebetween;

a supply of expansion fluid in fluid communication with the proximal end portion of the injection lumen, wherein the injection lumen, expansion chamber, and vacuum lumen define a fluid path for the flow of expansion fluid therethrough, and a supply of inflation fluid in fluid communication with the proximal end portion of the inflation lumen, wherein the inflation lumen and inflation chamber define a fluid path for the flow of inflation fluid therethrough.

23. The device according to claim 22, wherein the distal end of the injection lumen is sealed.

24. The device according to claim 22, wherein the inflation fluid is a cryogenic fluid.

25. The device according to claim 22, wherein the expansion fluid is a cryogenic fluid.

26. A medical device comprising:
an elongate shaft having proximal and distal end portions, the shaft defining or containing an injection lumen, an exhaust lumen, an inflation lumen, and a vacuum lumen therethrough, each lumen having a proximal end portion and distal end portion proximate the proximal and distal end portions of the shaft, respectively;

a first expandable membrane coupled to the distal end portion of the shaft, having an inner surface and an outer surface, the inner surface being in fluid communication with the distal end portion of the inflation and exhaust lumens to define an inflation chamber inside of the membrane a second expandable membrane having an inner surface and an outer surface, the inner surface being in fluid communication with the distal end portions of the injection and vacuum lumens, the second membrane being disposed around the first membrane to define an expansion chamber therebetween;

a supply of cryogenic fluid in fluid communication with the proximal end portion of the injection lumen, wherein the injection lumen, expansion chamber, and vacuum lumen define a fluid path for the flow of cryogenic fluid therethrough, and a supply of inflation fluid in fluid communication with the proximal end portion of the inflation lumen, wherein the inflation lumen, inflation chamber and exhaust lumen define a fluid path for the flow of inflation fluid therethrough.

* * * * *